(12) United States Patent
Sibbett

(10) Patent No.: US 9,518,985 B2
(45) Date of Patent: Dec. 13, 2016

(54) SEMI-QUANTITATIVE LATERAL FLOW ASSAYS

(71) Applicant: STC.UNM, Albuquerque, NM (US)

(72) Inventor: Scott A. Sibbett, Corrales, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/121,488

(22) Filed: Sep. 11, 2014

(65) Prior Publication Data

US 2015/0004594 A1 Jan. 1, 2015

Related U.S. Application Data

(63) Continuation of application No. PCT/US2013/000059, filed on Mar. 6, 2013.
(Continued)

(51) Int. Cl.
*G01N 21/75* (2006.01)
*G01N 33/543* (2006.01)
(Continued)

(52) U.S. Cl.
CPC ...... *G01N 33/54386* (2013.01); *G01N 33/558* (2013.01); *G01N 33/56988* (2013.01); *G01N 2333/005* (2013.01)

(58) Field of Classification Search
CPC .................. B01L 2300/87; B01L 2300/0864; G01N 33/54366; G01N 33/558; G01N 33/523; G01N 33/526; G01N 33/56988; Y10S 435/97; B01J 2219/00536
See application file for complete search history.

(56) References Cited

U.S. PATENT DOCUMENTS 5,766,961 A    6/1998  Pawlak et al. ................ 436/510
8,377,710 B2 * 2/2013  Whitesides .......... G01N 33/523
                                                  422/420
(Continued)

OTHER PUBLICATIONS

Sergio Mendez et a., "Imbibtion in Porous Membranes of Complex Shape: Quasi-stationary Flow in Thin Rectangular Segments", Langmuir 2010, 26(2), 1380-1385. published on web Oct. 21, 2009.
(Continued)

*Primary Examiner* — Dennis M White

(57) ABSTRACT

The present invention provides a semi-quantitative lateral flow assay device and method for generating semi-quantitative data from a lateral flow assay. The device comprises a thin, porous hydrophilic substrate wherein the substrate includes a star-shaped or other geometry taken in plan view having a liquid sample-receiving central region and multiple arms that extend or radiate out from the central region. Each arm includes a reaction zone formed by the presence of an analyte-capturing agent wherein the reaction zone of each arm is located at a different distance from the central region such that the analyte in the sample is captured accumulates in different quantities at at least some of the reaction zones of the arms in a manner that can be analyzed to yield semi-quantitative data from lateral flow assays. The reaction zones on the arms can be analyzed visually and/or by software analysis of a digital image based on color saturation, grayscale, or other characteristics of the reactions zones due to the presence of different amounts of analyte to produce semi-quantitative data of the total loading of a virus or other agent of interest of a patient's blood.

13 Claims, 2 Drawing Sheets

Related U.S. Application Data

(60) Provisional application No. 61/615,079, filed on Mar. 23, 2012.

(51) Int. Cl.
  *G01N 33/558* (2006.01)
  *G01N 33/569* (2006.01)

(56) References Cited

U.S. PATENT DOCUMENTS

| | | | |
|---|---|---|---|
| 2005/0214161 A1 | 9/2005 | Gupta et al. | 422/56 |
| 2007/0298433 A1* | 12/2007 | Sia | B01L 3/502707 435/7.1 |
| 2008/0317633 A1* | 12/2008 | Sibbett | B01L 3/5023 422/68.1 |
| 2009/0104630 A1 | 4/2009 | Reiter et al. | 435/7.21 |
| 2010/0041571 A1 | 2/2010 | Cohen et al. | 506/39 |

OTHER PUBLICATIONS

Erin M. Fenton et al., Multiplex Lateral-Flow Test Strips Fabricated by Two-Dimensional Shaping, Applied Materials & Interfaces, vol. 1, No. 1, 124-129, 2009 published on web Oct. 21, 2009.

\* cited by examiner

SEMI-QUANTITATIVE LATERAL FLOW ASSAYS

RELATED APPLICATION

This application claims benefits and priority of U.S. provisional application Ser. No. 61/615,079 filed Mar. 23, 2102, the disclosure of which is incorporated herein by reference.

FIELD OF THE INVENTION

The present invention relates to a semi-quantitative lateral flow assay device and method for generating semi-quantitative data from lateral flow assays.

BACKGROUND OF THE INVENTION

Current commercially available lateral flow test kits are limited to answering yes/no questions such as those concerning pregnancy or influenza. These tests are enabled by a layer of porous material, typically nitrocellulose, which, when wetted with an analyte-containing liquid sample at one end, produces a flow to dry areas by capillary action [Mendez, S.; Fenton, E. M.; Gallegos, G. R.; Petsev, D. N.; Sibbett, S. S.; Stone, H. A.; Zhang, Y.; López, G. P. *Langmuir* 2010, 26, 1380-1385]. Initially, the flow brings analyte into contact with a patch of lyophilized dye-tagged antibodies (also known as reporter molecules), thereby producing dye-tagged analyte-antibody complexes. These complexes are swept along with the flow. Further downstream, they are brought into contact with a second patch of antibodies, these being immobilized on the nitrocellulose at a defined reaction zone. The complexes are captured by the immobilized antibodies. If enough analyte is present in the original sample, it accumulates at the reaction zone to an extent that dye-tag is perceptible to the human eye and interpreted as a positive result [U.S. Pat. No. 5,766,961]. Below a certain threshold of analyte concentration in the original sample, no line is perceived, and the result is interpreted to be negative. Advantages of these tests are that they are relatively simple to perform and interpret, and relatively inexpensive to fabricate. However, to obtain quantitative or even semi-quantitative results, more sophisticated instruments are employed, especially the high-volume in vitro diagnostic tools that are ubiquitous in clinical reference laboratories today. Many important tests are quantitative in nature, such as HIV viral loading, the extent of liver function damage, and measurements of environmental exposure, and these cannot be answered at present by commercially available lateral flow assays.

SUMMARY OF THE INVENTION

The present invention provides a semi-quantitative lateral flow assay device and method for generating semi-quantitative data from a lateral flow assay.

In an illustrative embodiment of the present invention, the device comprises a thin, porous hydrophilic substrate wherein the substrate includes a star-shaped or other geometry, taken in plan view, having a liquid sample-receiving central region and multiple arms that extend or radiate out from the central region. Each arm includes a reaction zone formed by the presence of an analyte-capturing agent wherein the reaction zone of each arm is located at a different distance from the central region such that the analyte in the sample resides in different quantites at at least some of the reaction zones of the arms in a manner that can be analyzed to yield semi-quantitative data from the lateral flow assay. The reaction zones on the arms can be analyzed visually and/or by analysis of a digital image, based oh color saturation, grayscale, or other characteristics of the reactions zones to produce semi-quantitative data of the total loading of a virus or other agent of interest of a sample of a patient's blood. Periodic testing using the device can be employed to monitor the total viral or other loading over a given time; for example, to monitor the total viral loading of an AIDS patient's blood over time.

In a particular illustrative embodiment of the invention, the sample to be analyzed is typically deposited at the central region of a star-shaped geometry, where it flows by capillary action into all arms of the star and where it passes through and contacts with at least one reaction zone per arm. Analyte within the sample is captured and accumulates forming a visually perceptible line at the reaction zone of at least some of the arms. Each of the reaction zones is placed at a slightly different distance from the central region of the star geometry, typically in sequence, from arm to arm, from near to the central region to far from the central region. Hence from arm to arm, there is gradual variation in the total quantity of sample which is caused to contact a given reaction zone. The variation creates an overall reaction pattern comprising a gradual variation of reaction zone color, grayscale, or other characteristic proceeding from arm to arm that can be analyzed to yield the semi-quantitative data.

The above and other advantages of the invention will become more apparent from the following detailed description taken with the following drawings.

DETAILED DESCRIPTION OF THE INVENTION

The present invention provides a device and method for generating semi-quantitative data from a lateral flow assay wherein a thin, porous hydrophilic substrate, includes a star-shaped or other two-dimensional geometry (taken in plan view) having a liquid sample-receiving central region and multiple arms that extend or radiate out from the central region. The arms each include one or more reaction zones located at different locations relative to the central region in a manner that the analyte in a sample placed on the central region resides in different quantities at at least some, or all, of the reaction zones of the arms in a manner to produce a gradual variation of reaction zone color, grayscale or other characteristic from arm to arm and that can be analyzed to yield semi-quantitative data from the lateral flow assay. For purposes of illustration and not limitation, the variation of color, grayscale or other characteristic at the reaction zones can be analyzed visually and/or by software analysis of a digital image to produce semi-quantitative data of the total loading of a foreign agent (e.g. virus) of a patient's blood.

Other readout techniques to determine semi-quantitatively the amount of analyte captured can be employed. For example, in lieu of use of dye-tagged analyte, the invention envisions use of analyte tagged in other ways including, but not limited to, radio-labeled analyte, or magnetically-tagged, for which the readout would be by radiochemical or magnetic analysis. By semi-quantitative data is meant the measurement of a quantity of material, accurate to within a range of values.

Figure 1:
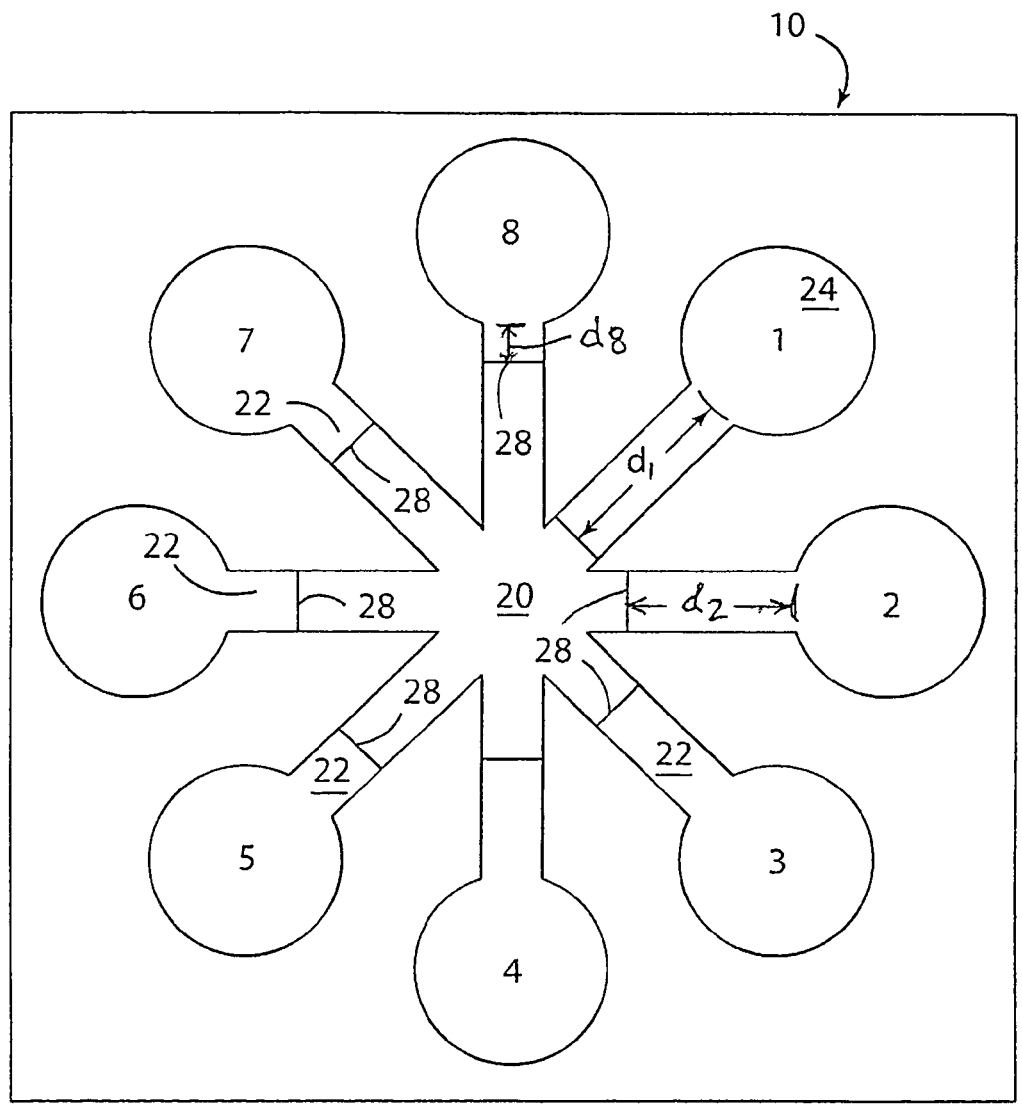
FIG. 1 is a plan view of a star-shaped lateral flow assay device pursuant to an illustrative embodiment of the invention fabricated by two-dimensional shaping.
Figure 2:
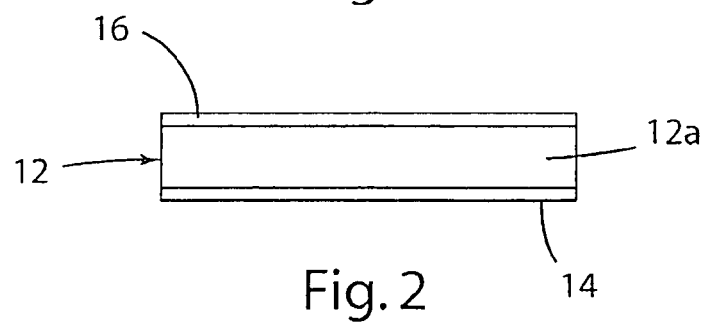
FIG. 2 is a sectional view of the device showing the porous layer on a backing layer with an optional covering layer to reduce evaporation.

Referring to FIGS. 1 and 2, an illustrative embodiment of the later al flow assay device 10 is shown as comprising a thin, porous hydrophilic substrate 12 comprising nitrocellulose or other suitable material. For purposes of illustration and not limitation, the substrate 10 can comprise a commercially available nitrocellulose sheet 12a of uniform 0.0002 inch thickness with a polyester backing layer 14 and an optional upper cover tape or layer 16, such as transparent vinyl cover tape adhesive (part no. GL-166-clear, G & L Precision Die Cutting, Inc., San Jose, Calif., USA) that can be applied after an unknown sample is deposited on a sample-receiving central region to reduce or prevent evaporation from the upper surface of the substrate. The substrate can have a thickness generally in the range of 100 to 200 microns for purposes of illustration and not limitation, although the invention is not limited to any particular substrate thickness.

In an illustrative embodiment, the device comprises, in plan view, a star-shaped two-dimensional geometry having liquid sample-receiving central region 20 and a plurality of arms 22 that extend or radiate out from the central region 20. In FIG. 1, the arms 22 each terminate in an optional circular outer region 24 that functions to increase the total quantity of analyte sampled per arm.

In FIG. 1, the arms can be spaced apart around the circumference or periphery of central region 20 to provide separate capillary flow paths for the liquid sample. The central region 20 typically has a circular shape in plan view as shown in FIG. 1, but can have other symmetrical shapes such as an n-sided polygon, where n is the number of arms. The number of arms 22 can be selected to provide a desired number of analyzable reaction zones 28 where analyte in the sample can be captured and accumulated at each reaction zone 28 on each arm. Each reaction zone includes an analyte-capturing agent that is appropriately selected to react, complex, retain, adsorb or otherwise capture the analyte of interest, if present in the liquid sample, at a given reaction zone. For example, in order to accumulate the AIDS virus in the sample of a typical AIDS patient's blood, the analyte-capturing agent can be an anti-HIV protein.

The analyte-capturing agent can be deposited or otherwise provided on each arm 22 to form a respective reaction zone 28 in the form of a narrow strip or line, FIG. 1, extending transversely across the width of each arm 22 as shown in FIG. 1 for purposes of illustration and not limitation. Other reaction zone shapes can be used however, and more than one reaction zone 28 can be provided on each arm 22.

Figure 3:
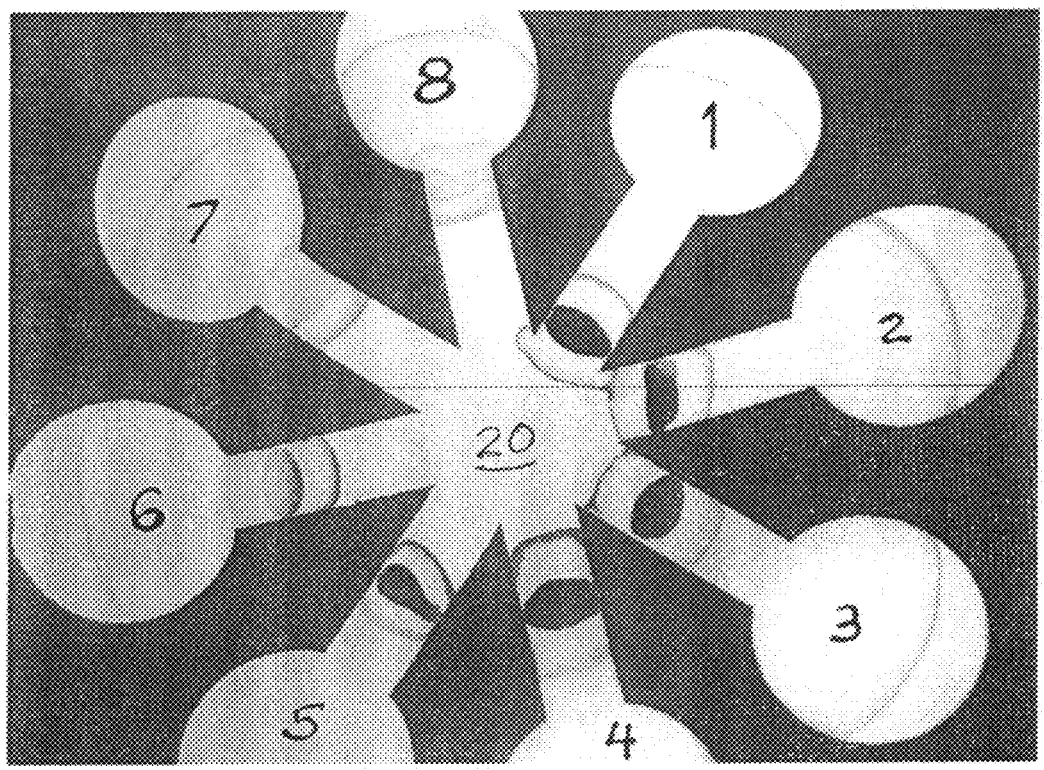
FIG. 3 is a photographic image of an 8-arm star-shaped lateral flow assay fabricated by two-dimensional shaping after a liquid sample to be analyzed has been deposited and travelled by capillary flow into the arms.

The reaction zone 28 of each arm 22 is located at a respective different distance $d_n$ where n is 1 to 8 (e.g. $d_1$ for arm 1, $d_2$ for arm 2, and so on for arms 4 through 8) relative to the central region 20 and adjacent arms as defined below and shown in FIG. 1. For purposes of illustration and not limitation, each reaction zone 28 is shown located at a slightly different respective distance relative to the central region 20 of the star geometry in sequence from far from the central region 20 (arm 8—FIG. 3) to near to the central region 20 (arm 1—FIG. 3) from arm to arm. Hence from arm to arm, there is gradual variation in the total quantity of sample which is caused to contact a given reaction zone 28. The variation of reaction zone color, grayscale or other characteristic creates an overall reaction pattern proceeding from arm to arm that can be analyzed to yield the semi-quantitative data. FIG. 3 illustrates an overall reaction pattern that resembles a spiral pattern from arm to arm.

In an exemplary embodiment of FIG. 1 offered for purposes of illustration and not limitation, the diameter of the central region 20 can be 1 cm and the dimensions of the eight arms 22 each can be 0.5 cm width and 5 cm length. These illustrative dimensions are selected to ensure complete capillary-action-driven wetting of all arms when applying a sample as small as approximately 100 microliters, but can be varied to accommodate smaller sample sizes The two-dimensional star-shaped geometry of the device can be formed, for example, by: (a) lithographic or other means of patterning hydrophobic regions on thin hydrophilic media, or (b) two-dimensional shaping with a knife, laser or other cutting device of thin hydrophilic porous media substrate. When the substrate is patterned by (a) without cutting, liquid impermeable barriers can be patterned by lithographic or other means on a single sheet substrate to define the central region 20 and multiple arms 22 without cutting.

The sample to be analyzed is typically deposited at the central region 20 of the star geometry, where it is drawn by capillary action into all arms of the star geometry, and where it passes through and contacts with at least one reaction zone 28 each per arm. Analyte within the sample is captured and accumulates and forms a visually perceptible line at the reaction zone 28 of at least some of the arms. Each of the reaction zones is placed at a slightly different distance from the center of the star geometry, typically in sequence from far from the center, to near to the center (FIG. 1). Hence from arm to arm, there is gradual variation in the total quantity of sample which is caused to contact a given reaction zone.

In the case of a reaction zone 28 positioned near the central region 20 of the star geometry, a relatively large quantity of sample flows across that reaction zone, and therefore is more likely to produce a bright line in the presence of analyte; whereas in the case of a reaction zone 28 positioned far from the central region 20 of the star geometry, only a relatively small quantity of sample flows across the reaction zone, and is therefore more likely to produce a faint or undetectable line in the presence of analyte. When the assay is employed in the presence of analyte, there is produced a continuous change in color saturation (color density) from arm to arm, from one reaction zone to the next, passing from imperceptible color to fully saturated color. To make a semi-quantitative determination of analyte concentration, either: (i) a digital image is recorded and analyzed by software; or (ii) the unaided human eye identifies the single arm in the radial sequence where color first appears; or both (i) and (ii). A digital image of the arms 22 can be made by a conventional imaging device, such as a optical scanner, digital camera or cell phone camera, and then analyzed by digital imaging software, such as the UTHSCA Image Tool (University of Texas Health Science Center, San Antonio, Tex.) for variation of color or grayscale.

Theory

The first step in typical lateral flow assays is to conjugate analyte A with dye molecule D* to produce dye-tagged molecule AD*. The second step is to capture AD* at a reaction zone comprised of an excess of immobilized capture sites C, which are usually antibodies. The reaction zone is usually shaped as a line, and oriented transverse to the lateral flow in order to maximize contact of the liquid sample with the capture sites of the reaction zone. AD* is scavenged from the sample solution and accumulates at the reaction zone:

$$C + AD^* \rightarrow CAD^* \quad (1)$$

For immunoasays, the efficiency of scavenging is typically high due to a high equilibrium constant of eq 1. Also, rapid diffusion of AD* to C is promoted by the mechanical constraint that all capillary flow crosses the reaction zone where the thickness of the porous layer is only about 130 microns. If CAD* accumulates at the reaction zone above a certain threshold of concentration, a visible line is perceived by the eye. Although the transmission and absorption of light tends to reduce the grayscale value of the line, both are neglected in the present analysis because: (i) the porous layer of the bilayer films studied here are only about 130 microns thick, thus absorptive losses are negligible; and (ii) when viewed in ordinary room lighting, the porous film is opaque, hence transmittance losses are negligible. Therefore, in ordinary room lighting the measured grayscale value of the line is assumed to be a simple function of the reflectance coefficient of the CAD* complex times the total number of CAD* complexes at the reaction zone:

$$R = k n_{CAD^*} \quad (2)$$

where R=reflectance, grayscale units; k=reflectance coefficient, grayscale units per mole; and $n_{CAD^*}$=moles of captured dye-tagged analyte.

When the number of dye molecules is in excess of the number of analyte molecules, and when the capture sites is in excess of the number of dye molecules:

$$n_c \gg n_{D^*} \gg n_A \quad (4)$$

where $n_C$=moles of capture sites; $n_{D^*}$=moles of dye tag; and $n_A$=moles of analyte. When scavenging by capture sites is efficient, then every analyte molecule is tagged and captured:

$$n_A \cong n_{CAD^*} \text{ and } R = k n_A \quad (5)$$

Upon depositing a liquid sample at the center of a symmetrical star pattern of homogeneous porous material, the sample flows equally to all n arms. Assuming perfect capture efficiency, the number of moles of analyte captured at the reaction zone of the nth arm is given by the equation:

$$n_{A,n} = d_n w h \emptyset [A]_0 \quad (6)$$

where: $d_n$=distance between the reaction zone and peripheral end of the nth arm, cm; w=width of arm, cm; h=thickness of porous material, cm; ø=porosity of porous material, %; and $[A]_0$=molarity of analyte in sample. Thus $$R_{A,d_n} = k d_n w h \emptyset [A]_0 \quad (7)$$

where $R_{A,d_n}$=reflectance due to analyte A at a reaction zone situated d cm from the peripheral end of arm n. A plot of $R_{A,d}$ versus dwhø $[A]_0$ is predicted to be linear with a slope of k and a y-intercept of zero.

The foregoing mathematical treatment also applies to the sort of simple color-forming reactions investigated here in which colorless analyte A reacts with immobilized C at the reaction zone to generate an immobilized colored product CA*:

$$C + A \rightarrow CA^* \quad (8)$$

Example of Device Fabrication and Operation

As an illustrative example, the device shown in FIG. 3 depicts results obtained from starch complexation by iodide ion, to form a blue-purple starch-pentaiodide complex. This particular illustrative device was fabricated by two-dimensional shaping of two mil (0.002") clear polyester-backed sheets of Hi-Flow Plus 135 nitrocellulose membranes (no. HF13502XSS; Millipore Corp., Billerica, Mass.). Two-dimensional shaping was performed with a computer-controlled X-Y knife cutter plotter (Graphtec FC7000-75, Western Graphtec Inc., Irvine, Calif., USA) to form an 8-arm star pattern [Fenton, E. M.; Mascarenas, M. R.; López, G. P.; Sibbett, S. S. ACS Appl. Mater. Interfaces, 2009, 1, 124]. Reaction zones were formed by depositing 5 ml aliquots of starch solution (C in eq. 1 and 8) as a line or strip across the width of each of the eight arms 1-8 at different distances $d_n$, and allowing the solutions to air dry.

Experimental runs were initiated by pipetting about 200 mL of iodide-containing solution to the central region of the star-shaped device, FIG. 3, and allowing capillary action to evenly distribute the solution to all eight arms. The flow of sample was spontaneous and immediate. Optionally, we cap our devices with liquid-impermeable cover tape to prevent evaporation of sample from the device surface.

Flow only occurred outwardly to un-wetted portions of the porous substrate, hence once a given arm filled completely, flow ceased, and no additional analyte reached the reaction zone (except by diffusion, which is negligible given the microscale thickness of the media). Several devices tested were completely filled within about 2 minutes, by which time development of color was complete. The devices were then allowed to air dry at least 60 min prior to readout.

FIG. 3 shows one of the tested devices and reveals that the blue-purple color developed at reaction zones 28 of arms 1 through 7, but not in arm 8. FIG. 3 also shows that the color development proceeds in a radial fashion: arm 8 shows no color; arm 7 shows the first indication of color, arms, and arms 6 through 1 show a continual increase in color density. The observed radial progression of color saturation is due to the continuous change in distance, $d_n$, between a given reaction zone and the peripheral end of an arm, as governed by the theory given above. In the case of the star geometry depicted in FIG. 3, the distance $d_n$ varies continuously from one arm to the next, beginning with arm 1 for which $d_1$ is longest at 2.8 cm, to arm 8 for which $d_8$ is shortest at 0.4 cm. In other words, the eight reaction zones were deposited to provide a general spiral reaction pattern. The reaction zone of arm 8 is very near the peripheral end of the arm, hence only a relatively small volume of analyte-containing sample solution is caused to flow past the reaction zone by capillary action. Indeed, in the experiment of FIG. 3, the quantity of analyte that flows past the reaction zone of arm 8 is too low to produce a line of color at that reaction zone that can be perceived by the unaided human eye. At the other extreme, the reaction zone of arm 1 is relatively far from the peripheral end of the arm, hence a relatively large volume of analyte-containing sample solution is caused to flow past the reaction zone. This produces a dark line due to the accumulation of a sufficient amount of iodine-starch complex at the reaction zone. The reaction zones of arms 2-7 are intermediate in position, thus intermediate volumes of sample are drawn past these reaction zones, which thereby produces intermediate levels of color development.

To read out the devices and obtain a semi-quantitative value or range of values of analyte concentration, a calibration curve of variation of color density or grayscale values versus analyte quantity is determined in advance of a particular assay or assays. The calibration curve is specific to the chemical and/or biological agent of interest, under the conditions of operating the device. The calibration curve can be used directly, as in the case of computer-based image processing of a digital image of a post-test device. Alternatively, the calibration curve can be used for constructing a color key, such as is used in reading standard glucose lateral flow colorimetric test strips. In this latter case, the unaided eye compares color density of one or more of the arm reaction zones 28, to the several printed color density patches of the color key, and based on this comparison, the user decides which printed patch is closest in density to that observed from the post-test device.

Alternatively, the user may gauge which arm reaction zone, in the sequence of n-arms from 1 to n, color is first perceived. The identity of this arm is then referred to a look-up table, where, based on the calibration curve, the arm number denotes a semi-quantitative value or range of values of analyte concentration.

Other data readout techniques to determine semi-quantitatively the amount of analyte captured can be employed. In lieu of use of dye-tagged analyte, the invention envisions use of analyte tagged in other ways including, but not limited to, radio-labeled analyte, or magnetically-tagged, for which the readout would be by radiochemical or magnetic analysis.

Although the present invention has been described above with respect to certain illustrative embodiments, those skilled in the art will appreciate that changes and modifications can be made thereto within the scope of the invention as set forth in the appended claims.

I claim:

1. A device for performing semi-quantitative lateral flow assay, comprising:
a porous hydrophilic substrate wherein the substrate includes, in plan view, a liquid sample-receiving central region and multiple arms that extend out from the central region, wherein each arm includes a localized reaction zone, and wherein the reaction zone of every arm is located at a different distance relative to the central region and to one another such that the analyte in the sample resides in different quantities at at least some of the reaction zones of the arms to collectively produce a reaction pattern on the device, which reaction pattern can be analyzed by the unaided human eye to yield semi-quantitative data from the lateral flow assay.

2. The device of claim 1 wherein the substrate has, in plan view, a star-shaped geometry with a circular central region and the multiple arms radiating out from the central region.

3. The device of claim 2 wherein the reaction zone of each arm is located at a different radial distance from the circular central region to produce a radially-variable reaction pattern.

4. The device of claim 1 wherein analyte-capturing material is present at each reaction zone.

5. The device of claim 4 wherein the analyte- capturing material is present as a strip extending across on each arm.

6. The device of claim 4 wherein the analyte-capturing material and analyte in the sample form a visually perceptive, colored zone at at least some of the reaction zones.

7. The device of claim 4 wherein the analyte-capturing material captures the AIDS virus.

8. The device of claim 6 wherein there is gradual variation of reaction zone color from arm to arm that can be analyzed to yield the semi-quantitative data.

9. The device of claim 1 wherein the substrate is nitrocellulose.

10. The device of claim 1 wherein the substrate has a lithographically-patterned central region and a plurality of lithographically-patterned arms.

11. The device of claim 1 wherein the substrate has a knife cut central region and a plurality of knife-cut arms.

12. The device of claim 1 wherein said multiple arms comprise more than two arms and wherein said distance varies continuously from arm-to-arm around the central region.

13. The device of claim 1 wherein said multiple arms comprise more than two arms equally spaced apart around the central region.

* * * * *